US006872868B1

(12) United States Patent
Wagner et al.

(10) Patent No.: US 6,872,868 B1
(45) Date of Patent: *Mar. 29, 2005

(54) TRANSGENIC MAMMALS

(75) Inventors: Thomas E. Wagner, Athens, OH (US); Peter C. Hoppe, Bar Harbor, ME (US)

(73) Assignee: Ohio University, Athens, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 08/449,285

(22) Filed: May 24, 1995

Related U.S. Application Data

(63) Continuation of application No. 08/068,314, filed on May 28, 1993, now abandoned, which is a continuation of application No. 07/390,741, filed on Aug. 8, 1989, now abandoned, which is a continuation of application No. 06/897,666, filed on Aug. 18, 1986, now Pat. No. 4,873,191, which is a continuation of application No. 06/607,754, filed on May 4, 1984, now abandoned, which is a continuation of application No. 06/273,239, filed on Jun. 12, 1981, now abandoned.

(51) Int. Cl.$^7$ .............................................. A01K 67/027
(52) U.S. Cl. ............................ 800/14; 800/15; 800/16; 800/17
(58) Field of Search ................. 800/DIG. 2; 435/172.3; 936/32, 53, 70, 71; 860/14, 15, 16, 17, 18, 25

(56) References Cited

U.S. PATENT DOCUMENTS

| | | | |
|---|---|---|---|
| 4,237,224 A | 12/1980 | Cohen et al. | |
| 4,468,464 A | 8/1984 | Cohen et al. | |
| 4,704,362 A | 11/1987 | Itakura et al. | |
| 4,740,470 A | 4/1988 | Cohen et al. | |

FOREIGN PATENT DOCUMENTS

WO         9222646         12/1992

OTHER PUBLICATIONS

Bentvelzen et al. (1972) J. Natl. Cancer Inst. 48, 1089–1094.*
Bakker et al., (1978) J. Animal Sci. 46, 1572–1580.*
Bennett et al. (1977) J. Animal Sci. 46, 768–775.*
Nelson et al. (1979) J. Animal Sci. 49, 1497–1500.*
Simms et al., (1978) J. Animal Sci. 46, 458–462.*
The Science of Providing Milk for Man, J. R. Campbell and R. T. Marshall, aus., McGraw–Hill Book Co., New York, 1975, Chapter 5, Evaluating Diary Cattle, pp. 90–106.*
Kim et al. (1978) J. Animal Sci. 46, 1648–1657.*
Krabill et al. (1978) J. Animal Sci. 1356–1359.*
Strojek et al. (1988) *Genetic Engineering: Principles and Methods,* Vol. 16, Plenum Press.*
Kappell et al., (1992) Current Op. Biotech. 3, 548–553.*
Wall (1996) Threiology 45, 57–68.*
Houdebine (1994) J. Biotech. 34, 269–287.*
*The Science of Providing Milk for Man,* J. R. Campbell and R. J. Marshall, aus., McGraw–Hill Book, Co., New York, 1975, "Chapter 5 Evaluating Dairy Cattle," pp. 90–106.*
Sharon et al., (1969) Nature 224, 707–709.*
Heideman, S. Transgenic Rats: A Discussion in *Transgenic Animals: Proceedings of the Symposium on Transgenic Technology in Med. and Agric.,* First et al., eds. Butterworth–Heineman, Boston, 1991, pp. 325–332.*
Gordon et al. (1980) Proced. Natl. Acad. Sci. 77, 7380–7384.*
Jaenisch et al. (1974) Proced. Natl. Acad. Sci. 71, 1250–1254.*
Jähner et al., Nature 287: 456–458 (1980).
Jaenisch, Proc. Natl. Acad. Sci. 73(4): 1260–1264 (1976).
Jaenisch et al., Proc. Natl. Acad. Sci. 71(4): 1250–1254 (1974).
Wilmut et al., New Scientist, 7 Jul. 1988, pp. 56–59.
Van Brunt, BioTechnology 6(10): 1149, 1151, 1152, 1154 (1988).
Wigler, M., et al., *Cell,* 11:223–232 (1977).
Mulligan et al., Nature Vol. 277, pp. 108–114, Jan. 11, 1979.
Goeddel et al., Nature Vol. 281, pp. 544–548. Oct 18, 1979.
Cline et al., Nature Vol. 284, pp. 422–425, Apr. 3, 1980.
Wigler, M., et al., *Cell,* 11:223–232 (1977).
Wigler, M., et al., *Cell,* 14:725–731 (1978).
Wigler, M., et al., *Prod. Natl. Acad. Sci. U.S.A.,* 76:1373–1376 (1979).
Capecchi, M., *Cell,* 22:479–488 (1980).
Brinster, R. L., *J. Exp. Med.,* 140:1049–1056 (1974).
Mintz, B., et al., *Proc. Natl. Acad. Sci. U.S.A.,* 72:3585–3589 (1975).
Papaioannou, V. E., et al., *Nature* 258:69–73 (1975).
Pellicer, A., et al., *Proc. Natl. Acad. Sci. U.S.A.,* 77:2098–2102 (1980).
Watanabe, T., et al., *Proc. Natl. Acad. Sci. U.S.A.,* 75:5113–5117 (1978).

(Continued)

*Primary Examiner*—Deborah Crouch
(74) *Attorney, Agent, or Firm*—Fish & Neave; James F. Haley, Jr.; Barbara A. Ruskin

(57) ABSTRACT

Genetic transformation of a zygote and the embryo and mature organism which result therefrom is obtained by placing or inserting exogenous genetic material into the nucleus of the zygote or into any genetic material which ultimately forms at least a part of the nucleus of the zygote. It is preferred that the exogenous genetic material be added to a pronuclei of the zygote and is particularly preferred that it be added to the male pronucleus of the zygote. Thereafter, the zygote is allowed to undergo differentiation and development into the organism. The genotype of the zygote and the organism which results therefrom will include the genotype of the exogenous genetic material and the exogenous genetic material will be phenotypically expressed.

The invention can be utilized in a variety of ways including, for example, animal and plant breeding to modify or create new species, it can be used in epigenetics and in the understanding and treatment of genetic diseases.

64 Claims, No Drawings

OTHER PUBLICATIONS

Illmensee, K. et al., *Proc. Natl. Acad. Sci. U.S.A.,* 75:1914–1981 (1978).
Gordon, et al., *Proc. Natl. Acad. Sci. U.S.A.* 77:7380–7384 (1980).
Gordon et al., *PNAS* USA Vol. 77, pp. 7380–7384, Dec. 1980.
Wigler et al., *Cell* Vol. 16, pp. 777–785, Apr. 1979.
Mulligan et al., Nature Vol. 277, pp. 108–114 Jan. 11, 1977.
Goeddel et al., Nature Vol. 281, pp. 544–548 Oct. 18, 1979.
Cline et al., Nature Vol. 284, pp. 422–425 Apr. 3, 1980.
Wigler et al. Cell Vol. 11, pp. 223–232 (1977).
Wigler et al. Cell Vol. 14, pp. 725–731 (1978).
Wigler et al., PNAS, USA Vol. 76, pp. 1373–1376 (1979).
Capecchi et al., Cell Vol. 22, pp. 479–488 (1980).
Briuster, J. Exp. Med. Vol. 140, pp. 1049–1056, (1974).
Mintz, et al., PNAS USA Vol. 72, pp. 3585–3589 (1975).
Papaioannou et al., Nature Vol. 258, pp. 69–73 (1975).
Pellicer et al., PNAS USA Vol. 77, pp. 2098–2102 (1980).
Watanabe et al., PNAS USA Vol. 75, pp. 5113–5117 (1978).
Illmensee et al., PNAS USA Vol. 75, pp. 1914–1981 (1978).
Jaenisch, PNAS USA Vol. 73, pp. 1260–1264 (1976).
Jahner et al., Nature Vol. 287, pp. 456–458 (Oct. 1980).
Jaenish et al., PNAS Vol. 71, pp. 1250–1254 (Apr. 1974).
Lacy et al., Cell Vol. 18, pp. 1273–1283 (Dec. 1979).
Lacy et al., Cell Vol. 21, pp. 545–553 (Sep. 1980).
Hardison et al., Cell Vol. 18, pp. 1285–1297 (Dec. 1979).
Wagner et al., PNAS USA Vol. 78, pp. 6376–6380, Oct. 1981.
Mike G. Cordingley et al., "Transcription and Translation of the Herpes Simplex Virus Type 1 Thymidine Kinase Gene after Microinjection into Xenopus laevis Oocytes", J. General Virology, 54:409–414, (1981).
Jan Abramczuk et al., "Tumor Induction by Simian Virus 40 in Mice is Controlled by Long Term Persistence of the Viral Genome and the Immune Response of the Host", Journal of virology, Feb. 1984, pp. 540–548.
Paul Krimpenfort et al., "Generation of Transgenic Dairy Cattle Using In Vitro Embryo Production", Biotechnology, 9:844–846, Sep. 1991.
Robert Craigie et al., "The IN Protein of Moloney Murine Leukemia Virus Processes the Viral DNA Ends and Accomplishes Their Integration In Vitro", Cell, 62:829–837, Aug. 1990.
S. M. Willadsen, "A Method for culture of Micromanipulated Sheep Embryos and Its Use to Produce Monozygotic Twins", Nature, 277:298–300, Jan. 1979.
K. J. Betteridge, "An Historical Look at Embryo Transfer", Journal of Reproduction & Fertility, 62:1–12, 1981.
R. Brinster, "Carbon Dioxide Production from glucose by the Preimplantation Rabbit Embryo", Experimental Cell Research, 51:330–334, 1968.
P. F. Kraicer et al., "Interference Contrast Microscopy of Living Human Oocytes", Israel J. Med. Science, Vol. 7, No. 11, pp. 1298–1301, (1971).
A. Tsafriri et al., "The Time Sequence of Ovum Maturation in the Rat", J. Reprod. Fert., 29:387–393, (1972).
Henderson MAR, "Radial Cortical Fibers and Pronuclear Migration in Fertilized and Artificially Activated Eggs of Lytechinus Pictus", Developmental Biology, 78:1–13, (1980).
Mel Kunkle et al., "Cytological Events Leading to the Cleavage of Golden Hamster Zygotes", J. Morph. 146:197–214.

B. Nitsch et al,. "Simple Methods for Observing Cortical Granules in Living Mammalian Egges", Experientia, Vol. 33, No. 9, pp. 1252–1253, (1977).
B. N. Day, "Embryo Transfer in Swine", Theriogenology, Vol. 11, No. 1, pp. 27–31, Jan. 1979.
Everett Anderson, "A Cytological Study of the Centrifuged Whole, Half, and Quarter Eggs of the Sea Urchin Arbacia puntulata", The Journal of Cell Biology, 47:711–733, (1970).
R. H. Foote et al., "Superovulation, Ovum Collection, Culture and Transfer. A Review", Journal of Dairy Science, Vol. 53, No. 12, pp. 1681–1692.
R. J. Wall et al., "Development of Porcine Ova that were Centrifuged to Permit Visualization of Pronuclei and Nuclei", Biology of Reproduction, 32:645–651, (1985).
J. P. Selgrath et al., "Collection and Transfer of Microinjectable Embryos from Dairy Goats", Theriogenology Vol. 34, No. 6, pp. 1195–1205, Dec. 1990.
Robert E. Hammer et al., "Genetic Engineering of Mammalian Embryos", Journal of Animal Science, 63:269–278, (1986).
Peter C. Hoppe, et al., "Fertilization in vitro and Development of Mouse Ova", Biology of Reproduction, 8:420–426, (1973).
Robert E. Hammer et al., "Production of Transgenic Rappits, Sheep and Pigs by Microinjection", Nature, 315:680–683.
Brigid Hogan et al., "Manipulating the Mouse Embryo", A Laboratory Manual, pp. 136–141, 303.
Jan Abramczuk et al., "Attempts of Permanent Introduction of SV40 Genome into Mouse Gametes and Early Embryos", *Manipulation and Expression of Genes in Eukaryotes,* pp. 335–358 Academic Press, Australia, 1983.
Ralph A. Sorensen, Cinemicrography of Mouse Oocyte Maturation Utilizing Nomarski Differential–Interference Microscopy.
K. R. Bondioli, et al., "Production of Transgenic Cattle by Pronuclear Injection", pp. 265–273.
Beatrice Mintz, "Allphenic Mice of Multi–Embryo Origin", *Method Mammalian Embryology,* ed. Daniel J. Freeman Co., San Francisco, pp. 186–214.
Keen A. Rafferty, Jr., *Methods in Experimental Embryology of the Mouse,* The John Hopkins Press, pp. 15–92, (1970).
R. L. Brinster, "Cultivation of the Mammalian Embryo", *Growth, Nutrition & Metabolism of Cells in Culture,* Vol. 2, eds. Rothblat et al., Academic Press, New York, N.Y., pp. 251–286, 1972.
B. G. Brackett et al., "Uptake of Heterologous Genome by Mammalian Spermatozoa and Its Transfer to Ova through Fertilization", Proceedings of the National Academy of Sciences, Vol. 68, No. 2, pp. 353–357, Feb. 1971.
G. V. Cortner, et al., "Phase Contrast Microscopy versus Differential Interference Contrast Microscopy as Applicable to the Observation of Spermatozoa", *Journal of Forensic Sciences,* pp. 830–832.
J. W. Gordon et al., Gene Transfer into Mouse Embryos: Production of Transgenic Mice by Pronuclear Injection, pp. 411–433 (1983).
Buhler, et al., *Rabbit β–Casein Promoter Directs Secretion of Human Interleukin–2 the Milk of Transgenic Rabbits,* Bio/Technology, vol. 8, pp. 140–143, Feb. 1990.
Clark, et al., *Germ Line Manipulation: Applications in Agriculture and Biotechnology* Transgenic Animals, ch. 11, pp. 248–270, 1992.

Durnam, et al., *Transcriptional Regulation of the Mouse Metallothionein–I Gene by Heavy Metals,* The Journal of Builogical Chemistry, vol. 256, no. 11, pp. 5712–5716. Jun. 10, 1981.

Fabricant, et al., *Gene Transfer in Goats,* THERIOGENOLOGY, vol. 27, no. 1, p. 229.

Ganten, et al., *Species Specificity of Renin Kinetics in Transgenic Rats Harboring the Human Renin and Angiotensinogen Genes,* Proc. Natl. Acad. Sci. USA, vol. 89, pp. 7806–7809, Aug. 1992.

Hammer, et al., *Spontaneous Inflammatory Disease in Transgenic Rats Expressing HLA–B27 and Human $\beta_2 m$: An Animal Model of HLA–B27–Associated Human Disorders,* Cell, vol. 63, pp. 1099–1112, Nov. 30, 1990.

Hammer, et al., *Production of Transgenic Rabbits, Sheep and Pigs by Microinjection,* Nature, vol. 315, pp. 680–683, Jun. 1985.

Hochi, et al., *Secretion of Bovine α–Lactalbumin Into the Milk of Transgenic Rats,* Molecular Reproduction and Development, vol. 33, pp. 160–164, 1992.

Hochi, et al., *Successful Production of Transgenic Rats,* Animal Biotechnology, vol. 1(2), pp. 175–184, 1990.

Knight, et al., *Transgenic Rabbits with Lymphocytic Leukemia induced by the c–myc Oncogene Fused with the Immunoglobulin Heavy Chain Enhancer,* Proc. Natl. Acad. Sci. USA, vol. 85, pp. 3130–3134, May 1988.

Martin, et al., *Production of Transgenic Swine,* Transgenic Animal Technology, ch. 11, pp. 315–355, 1994.

Mullins, et al., *Transgenesis in Nonmurine Species,* HYPERTENSION, vol. 22, no. 4, pp. 630–633, Oct. 1993.

Mullins, et al., *Fulminant Hypertension in Transgenic Rats Harbouring the Mouse Ren–2 Gene,* Nature, vol. 344, pp. 541–544, Apr. 5, 1990.

Pinkert, et al., *Enhanced Growth Performance in Transgenic Swine,* Transgenic Animals, Chapters 20–25, pp. 251–324, 1991.

Polge, et al., *Induced Expression of a Bovine Growth Hormone Construct in Transgenic Pigs,* pp. 189–199 in Heap, et al. . . . , Biotechnology in Growth Regulation 1989.

Robl, et al., *Production of Transgenic Rats and Rabbits,* Transgenic Animal Technology, chapter 9, pp. 265–277, 1994.

Roschlau, et al., *Gene Transfer Experiments in Cattle,* J. Reprod. Fert. Suppl., vol. 38, pp. 153–160, 1989.

Selgrath, et al., *Collection and Transfer of Microinjectable Embryos from Dairy Goats,* THERIOGENOLOGY, vol. 34, no. 6, pp. 1195–1205, Dec. 1990.

Simons, et al., *Alteration of the Quality of Milk by Expression of Sheep β–Lactoglobulin in Transgenic Mice,* Nature, vol. 328, pp. 530–532, Aug. 1987.

Smith, et al., *Tissue–Specific Expression of Kallikrein Family Transgenes in Mice and Rats,* vol. 11, no. 5, pp. 345–358, 1992.

Swanson, et al., *High Level Expression of Human Apolipoprotein A–I in Transgenic Rats Raises Total Serum High Density Liproprotein Cholesterol and Lowers Rat Apolipoprotein A–I ,* Transgenic Research, vol. 1, pp. 142–148, 1992.

Velander, et al., *High–Level Expression of a Heterologous Protein in the Milk of Transgenic Swine using the cDNA Encoding Human Protein C,* Proc. Natl. Acad. Sci, USA, vol. 89, pp. 12003–12007, Dec. 1992.

Wagner, et al., *The Possibility of Transgenic Livestock,* Theriogenology, vol. 21, no. 1, pp. 29–44, Jan. 1984.

Vitale, et al., *Generation of Alzheimers Precursor Protein Transgenic Rats,* THERIOGENOLOGY, vol. 39, pp. 334, 1993.

Wall, et al., *High–Level Synthesis of a Heterologous Milk Protein in the Mammary Glands of Transgenic Swine,* Proc. Natl. Acad. Sci. USA, vol. 88, pp. 1696–1700, Mar. 1991.

Hayes, et al., *Development of Brain Tumors in Mice Transgenic for the Neu Oncogene under the Transcriptional Control of the Myelin Protein Gene,* Transgenes, Development and Disease, Abstract B303, p. 194.

Hully, et al., *Transgenic Hepatocarcinogenesis in the Rat,* Transgenes, Development and Disease, Abstract B304, p. 194.

Minhas, et al., *Visualization of Pronuclei in Living Bovine Zygotes,* Biology of Reproduction, vol. 30, pp. 687–691, 1984.

Church, R. B. *Embryo Manipulation and Gene Transfer in Domestic Animals,* Tibtech, vol. 5, pp. 13–19, Jan. 1987.

Swift, G. H., Hammer, R. E., MacDonald, R. J., and Brinster, R. L. Cell 38: 639–646 (1984).

Ornitz, D. M., Palmiter, R. D., Manner, R. E., Brinster, R. L. Swift, G. H., and mcDonald, R. J., Nature 313: 600–602 (1986).

Shani, M. Nature 314: 283–286 (1985).

Townes, T. M., Lingrel, J. B., Chen, H. Y., Brinster, R. L., Palmiter, R. D. Embo, J. 4: 1715–1723 (1985).

Chada, K., Magram, J., Raphal, K., Radice, G., Lacy, E., Constantini, R. Nature 314: 377–380 (1985).

Hanahan, D. Nature 315: 115–122 (1985).

Overbeek, P. A., Chepelinsky, A. B., Khillan, J. S. Piatigorsky, J., Westphal, H. Proc. Natl. Acad. Sci. USA 82: 7815–7819 (1985).

Khillan, J. S., Schmidt, A., Overbeek, P. A., Crombrugghe, B., Westphal, H. Proc. Natl. Acad. Sci. USA 83: 725–739 (1986).

Lepsant, J. A., Pictet, R., Jami, J. Proc. Natl. Adac. Sci. USA 83: 2511–2515 (1986).

Andres, A. C., Schonenberger, C. A. Groner, B., Hennighausen, L., LeMeur, M., Gerlinger, P. Proc. Natl. Acad. Sci. USA 84: 1299–1303 (1987).

Stewart, T. A., Pattengale, P. K., Leder, P. Cell 38: 627–637 (1984).

Brinster, R. L., Chen, H. Y., Trumbauer, M. E., Yagle, M. K., Palmiter, R. D. Nature 306: 332–336 (1983).

Small, J. A., Scangos, G. A., Cork, L., Jay, g., Khoury, G. Cell 46: 13–18 (1986).

Harbers, K., Kuehn, M., Delius, H., Jaenisch, R. Proc. Natl. Acad. Sci. USA 81: 1504–1508 (1984).

Land, R. A., Metcalf, D., Cuthbertson, R. A., Lysons, I., Stanley, E., Kelso, A., Kannourakis, G., Williamson, D. J., Klintworth, G. K., Gonda, T. J., Dunn A. R. Cell 51: 675–686 (1987).

Epstein, C. J., Avraham K. B., Lovett, M., Smith, S., Elroy–Stein, O., Rotman, G., Bry, C., Groner, Y. Proc. Natl. Aca. Sci. USA 84: 8044–8048 (1987).

Gordon, K., Lee, E., Vitale, J. A., Smith, A. E.,Westphal, H., Hennighause, L. Biotechnology 5: 1183–1187 (1987).

Popko, B., Puckett, C., Lai, E., Shine, H. D. Readhead, C., Takahasi, N., Hunt, S. W. III., Sidman, R. L., Hood, L. Cell 48: 713–721 (1987).

Lacey, M., Alper, A., Hanahan, D., Nature 322: 609–612 (1986).

Ruther, U., Garber, C., Komtowski, D., Muller, R., Wagner, E. F. Nature 325: 412–416 (1987).

S. Tonegawa, S., Kishimoto, T., Nature 316: 67–69 (1985).

Palmiter, R. D., Brinster, R. L., Hamer, R. E., Trumbauer, M. E., Rosenfeld, M. G., Birnberg, N. E., Evans, R. M., Nature 300: 611–615 (1982).

Sterwart, T. A., Science 234: 1372–1378 (1986).

Simmons, J. P., McClenaghan, M., Clark, J. A., Nature 328: 530–532 (1987).

Palmiter, R. D., Norstedt, G., Gelinas, R. E., Hammer, R. E., Brinster, R. S. Science 222: 809–814 (1983).

McKnight, G. S., Hammer, R. E., Kuenzel, E. A., Brinster, R. L., Cell 34: 355–341 (1983).

Brinster, R. L., Chen, J. Y., Mesisng, A., Van Kyde, T., Levine, A. J., Palmiter, R. D. Cell 37: 367–379 (1984) 22a Messing, A., Chen, J. Y., Palmiter, R. D., Brinster, R. L., Nature 316: 461–463 (1985).

Goring, D. R., Rossant, J., Clapoff, S., Breitman, M. L., Tsui, L. C., Science 235: 456–458 (1987).

Chisari, F. V., Pinker, C. A., Milich, D. R., Filippi, P., McLachlan, A., Palmiter, R. D., Brinster, R. L., Science 240: 1157–1163 (1985).

Hammer, R. E., Brinster, R. L., Rosenfeld, M. G., Evans, R. M., Mayo, K. E., Nature 315: 413–416 (1985).

Ebert, et al., Bio/Technology, 9: 835–838 (Sep. 1991).

Jaenisch, Rudolf, Science, 240: 1468–1473 (Jun. 1988).

* cited by examiner-

TRANSGENIC MAMMALS

This application is a continuation of application Ser. No. 08/068,314, filed May 28, 1993 now abandoned; which is a continuation of application Ser. No. 07/390,741, filed Aug. 8, 1989, now abandoned; which is a continuation of Ser. No. 06/897,666, filed Aug. 18, 1986, now U.S. Pat. No. 4,873,191; which is a continuation of Ser. No. 06/607,754, filed May 4, 1984, now abandoned; which is a continuation of Ser. No. 06/273,239, filed Jun. 12, 1981, now abandoned; all of which are hereby incorporated by reference.

TECHNICAL FIELD

The present invention relates to the field of genetics and methods of altering the genetic material of an organism. The invention has a wide variety of applications, for example, in animal and plant breeding, including transgenosis, in the field of epigenetics, which deals with the variation in gene expression during differentiation and development of eucaryotic organisms, and in the understanding and treatment of genetic diseases.

1. Background Art
2. Prior Art Statement

The possibility of transferring specific functional genes from one species to another has intrigued scientists for years. However, such transfers have only been realized in cell culture systems. Cloned rabbit β-globin gene sequences have been stably introduced into thymidine kinase (TK) deficient mutant mouse cells by DNA mediated cotransformation using the rabbit β-globin gene and herpes virus TK gene sequences, Wigler, M., et al, *Cell,* 11:223–232 (1977). This approach has been extended to use cellular TK, Wigler, M., et al, *Cell,* 14:725–731 (1978), adenine phosohoribosyl transferase, Wigler, M., et al, *Proc. Natl. Acad. Sci. U.S.A.,* 76:1373–1376 (1979), and hypoxanthine phosphoribosyl transferase, Graf, L. H., et al, *Som. Cell Genet.,* 5:1031–1044 (1979), genes as unlinked but selectable markers. Additionally, the use of a mutant hamster gene, which codes for an altered dihydrofolate reductase, as a selectable marker offering methotrexate resistance, allows the introduction and amplification of a broad range of genetic elements into a variety of cell lines, Wigler, M., et al, *Proc. Natl. Acad. Sci. U.S.A.,* 77:3567–3570 (1980). Although these cotransformation experiments enable a direct gene transfer between mammalian species to be effected, these techniques are all restricted to cell culture systems wherein only one cell in $10^5$–$10^7$ is transformed which requires that the transformed cells be selected for on restrictive media.

The direct microinjection of DNA has been used to introduce. Herpes Simplex virus TX gene into cultured mammalian cells. Capecchi, M., *Cell,* 22:479–488 (1980). However, the efficiency of transformation was extremely low even when the small pBR 322/TK DNA was coinjected with SV40 DNA, i.e., 15 transformants per 1,000 cells injected. Additionally, this technique does not result in the production of a mature organism much less one that could exhibit a phenotypic alteration.

Mosaic mice have been constructed by the injection of teratocarcinoma cells into the blastocysts of developing mice. Brinster, R. L., *J. Exp. Med.,* 140:1049–1056 (1974) Mintz, B., et al, *Proc. Natl. Acad. Sci. U.S.A.,* 72:3585–3589 (1975) and Papaioannou, V. E., et al, *Nature,* 258:69–73 (1975). Teratocarcinoma cells have also been used as vehicles for introducing genes into mice to produce mosaic mice. Pellicer, A., et al, *Proc. Natl. Acad. Sci. U.S.A.,* 77:2098–2102 (1980), Watanabe, T., et al, *Proc. Natl. Acad. Sci. U.S.A.,* 75:5113–5117 (1978) and Illmensee, K., et al *Proc. Natl. Acad. Sci. U.S.A.,* 75:1914–1981 (1978). However, by definition, a mosaic mouse has patches. of different, mutually exclusive genotypes and/or phenotypes. Additionally, the possibility of germ-line transmission with mosaic mice is reduced due to the fact that teratoma cells of XX chromosomal constitution cannot make sperm in mice that develop as males.

Recently, Gordon, et al, *Proc. Natl. Acad. Sci. U.S.A.,* 77:7380–7384 (1980), have observed TK genes in mice developed from embryos microinjected with the TK gene incorporated into a chimeric SV40 viral vehicle. These mice, however, did not express the TK gene product. In these experiments, as well as the experiments relating to the use of teratocarcinoma cells, no phenotypic alteration of the test animal was accomplished. The results reported by Gordon, et al, are not surprising since the SV40 virus has previously been shown to be functionally and genetically inactive when introduced into mouse embryos. Jaenisch, R. et al, *Proc. Natl. Acad. Sci. U.S.A.,* 71:1250–1254 (1974).

DISCLOSURE OF THE INVENTION

Genetic transformation of a zygote and the embryo and mature organism which result therefrom is obtained by the placing or insertion of exogenous genetic material into the nucleus of the zygote or to any nucleic genetic material which ultimately forms a part of the nucleus of the zygote. The genotype of the zygote and the organism which results from the zygote will include the genotype of the exogenous genetic material. Additionally, the inclusion of the exogenous genetic material in the zygote will result in a phenotypic expression of the exogenous genetic material. The genotype of the exogenous genetic material is expressed upon the cellular division or the zygote. However, the phenotypic expression, e.g., the production of a protein product or products of the exogenous genetic material or alteration of the zygote's or organism's natural phenotype, will occur at that point of the zygote or organism's development during which the particular exogenous genetic material is active. Alteration of the expression of a phenotype includes an enhancement or diminishment in the expression of a phenotype or an alteration in the promotion and/or control of a phenotype including the addition of a new promotor and/or controller or supplementation of an existing promotor and/or controller of a phenotype.

The present invention has application in the genetic transformation of multicellular eucaryotic organisms which undergo syngamy, i.e., sexual reproduction by the union of gamete cells. Examples of such organisms include amphibians, reptiles, birds, mammals, bony fishes, cartilaginous fishes, cyclostomes, arthropods, insects, mollusks, thallophytes, embryophytes including gymnosperms and angiosperms. Preferred organisms include mammals, birds, fishes, gymnosperms and angiosperms.

The invention is particularly useful in the breeding of plants and animals, especially ones of agricultural value, to obtain species having a genetic makeup which results in a plant or animal having more desirable characteristics. Since the source of the exogenous genetic material can be from animals or plants, synthetic equivalents of naturally occurring genetic material or totally new synthetically produced genetic material and from the same or a different species of the zygote being transformed, the invention can be used to modify a species or create a new species. Modification of a species is obtained when the genotype of the exogenous genetic material occurs in the genotype of the species whose zygote is being genetically transformed. A new species is obtained when the genotype of the exogenous genetic material occurs in another species and does not naturally occur in the species of the zygote being genetically transformed. For example, increased growth rate and the efficiency of feed utilization can be obtained by genetic transformation of animals used to produce meat. As an example, the genes relating to growth rate and feed utilization can be transferred from a buffalo into beef cattle which would create a new species. Dairy animals can undergo an increase in milk production and efficiency of feed utilization by transferring exogenous genetic material from species or breeds of the same species which have either or both traits. The quality and flavor of meat, for example, lamb, can also be enhanced in a similar manner. Additionally, the invention can be used as an in vivo analysis of gene expression during differentiation and in the elimination or dimunition of genetic diseases, e.g., hemophilia, Tay-Sachs disease, phenylketonuria, homocystinurea, galactosemia, thalassemia and sickle cell anemia.

EMBODIMENTS OF THE INVENTION

The following definition of biological and genetic terms will be useful in understanding this invention:

"Zygote" is a diploid cell having the potential for development into a complete organism. The zygote can result from parthenogensis, nuclear transplantation, the merger of two gametes by artificial or natural fertilization or any other method which creates a diploid cell having the potential for development into a complete organism. The origin of the zygote can be from either the plant or animal kingdom.

"Parthenogenesis" is any technique that allows for the development of a female or male gamete into a cell and its development into an organism which technique is different from the natural development of female and male gametes.

"Genetic material" is a material containing any DNA sequence or sequences either purified or in a native state such as a fragment of a chromosome or a whole chromosome, either naturally occurring or synthetically or partially synthetically prepared DNA sequences, DNA sequences which constitute a gene or genes and gene chimeras, e.g., created by ligation of different DNA sequences. Genetic material does not include DNA sequences incorporated in or carried by a plasmid, virus or phage.

"Exogenous genetic material" is genetic material not obtained from or does not naturally form a part of the specific germ cells or gametes which form the particular zygote which is being genetically transformed.

"DNA sequence" is a linear sequence comprised of any combination of the four DNA monomers, i.e., nucleotides of adenine, quanine, cytosine and thymine, which codes for genetic information, such as a code for an amino acid, a promoter, a control or a gene product. A specific DNA sequence is one which has a known specific function, e.g., codes for a particular polypeptide, a particular genetic trait or affects the expression of a particular phenotype.

"Gene" is the smallest, independently functional unit of genetic material which codes for a protein product or controls or affects transcription and comprises at least one DNA sequence.

"Genotype" is the genetic constitution of an organism.

"Phenotype" is a collection of morphological, physiological and biochemical traits possessed by a cell or organism that results from the interaction of the genotype and the environment.

"Phenotypic expression" is the expression of the code of a DNA sequence or sequences which results in the production of a product, e.g., a polypeptide or protein, or alters the expression of the zygote's or the organism's natural phenotype.

"Chromosome" is a fiber or threadlike structure which is completely or partially composed of genetic nucleic acid.

"Chromosomal material" is comprised of portions of or whole native chromosomes, isolated metaphase chromosomes (Wray, W., et al, *Exp. Cell Res.*, 59:469–478 (1970)) or artificial chromosomes composed of native or modified histone or protamine chromosomal core complexes and DNA. Artificial chromosomes can be prepared, for example, by removing a portion of the naturally occurring DNA sequences of a native chromosome and replacing it with new DNA sequences. Examples of such techniques are taught in Shewmaker, et al, *Eur. J. Biochem.*, 107:505–510 (1980) and Cohen, et al, *Eur. J. Biochem.*, 107:511–518 (1980).

Genetic transformation of a zygote and the organism which matures therefrom is obtained by the addition of exogenous genetic material in a manner such that the exogenous genetic material becomes a part of the nucleic portion of a zygote prior to division of the zygote. If the exogenous genetic material is added after mitosis or cellular division of the zygote, the exogenous genetic material must be added to each resulting nucleus. However, then there is the possibility that the exogenous genetic material may not be integrated into and become a part of the genetic material of the zygote and the organism which results therefrom. Thus, the exogenous genetic material can be added to any nucleic genetic material which ultimately forms a part of the nucleus of the zygote, including the zygote nucleus. The nucleic genetic material must be in a physical state which enables it to takeup the exogenous genetic material. There are numerous ways for accomplishing this. For example, the exogenous genetic material can be placed in the nucleus of a primordial germ cell which is diploid, e.g., a spermatogonium or oogonium. The primordial germ cell is then allowed to mature to a gamete which is then united with another gamete or source of a haploid set of chromosomes to form a zygote.

The exogenous genetic material can be placed in the nucleus of one of the gametes, e.g., a mature sperm, egg or polar body, which forms a part of the zygote. In this instance, if the exogenous genetic material is placed in the mature sperm prior to fertilization, the sperm cell should be induced to undergo decondensation. Otherwise, the chromosomal complement of the sperm cell is too dense to allow the addition of any material to its nucleus. Techniques for the decondensation are known in the art. Examples of such techniques can be found in Mahi, D. A., et al, *J. Reprod. Fert.*, 44:293–296 (1975); Hendricks, D. M. et al, *Exptl. Cell Res.*, 40:402–412 (1965); and Wagner, T. E., et al, *Archives of Andrology*, 1:31–41 (1978). Decondensation through the use of a disulfide reductant is preferred. The sperm cell into which the exogenous genetic material is placed is thereafter placed in the egg to enable the formation of the zygote.

The exogenous genetic material can be placed in the nucleus of a mature egg. It is preferred that the egg be in a fertilized or activated, by parthenogenesis, state. After the addition of the exogenous genetic material, then a complementary haploid set of chromosomes, e.g., a sperm cell or polar body, is added to enable the formation of a zygote.

When a polar body is used to diploidize a haploid egg, the exogenous genetic material can be placed in the polar body.

It is preferred that the exogenous. genetic material be placed in either the male or female pronucleus of the zygote. More preferably, it is placed in either the male or the female pronucleus as soon as possible after the sperm enters the egg. In other words, right after the formation of the male pronucleus when the pronuclei are clearly defined and are well separated, each being located near the zygote membrane. The male pronucleus is the preferred site for addition of the exogenous genetic material. When the exogenous genetic material is inserted into the female pronucleus, it is preferred that the exogenous genetic material be chromosomal material, more preferably that the chromosomal material be comprised of histone chromosomal core complexes and DNA, which can be artificial chromosomal material reconstituted from DNA sequences of native or modified histone chromosomal core complexes.

It is most preferred that the exogenous genetic material be added to the male DNA complement, or a DNA complement other than the DNA complement of the female pronucleus, of the zygote prior to its being processed by the ovum nucleus or the zygote female pronucleus. It is though. that the ovum nucleus or female pronucleus release molecules which affect the male DNA complement, perhaps by replacing the protamines of the male DNA with histones, thereby facilitating the combination of the female and male DNA complements to form the diploid zygote. Thus, for the purposes of this invention, the processing of a DNA complement by the female pronucleus of the zygote refers to a biochemical effect the female pronucleus has on the DNA complement prior to the physical contact between the pronuclei or between the female pronucleus and the particular DNA complement. Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material could then be added to the ovum or the decondensed sperm could be added to the ovum with the exogenous genetic material being added as soon as possible thereafter. Even when the DNA complement to the ovum DNA is of a female source, it is preferred that the exogenous genetic material be added to that female DNA complement shortly after its placement within the ovum or prior to its placement in the ovum in order to allow that DNA complement to be processed by the female pronucleus.

For the purposes of this invention a zygote is essentially the formation of a diploid cell which is capable of developing into a complete organism. Generally, the zygote will be comprised of an egg containing a nucleus formed, either naturally or artifically, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. Obviously, more exogenous genetic material can be added if it is exchanged for existing genes. Then, to a certain extent, the amount added is unlimited as long as the number of existing genes being removed is equal to the number inserted. However, the physical effects of deletion and addition must not be so great as to physically destroy the viability of the zygote. The biological limit of the number and variety of DNA sequences will vary depending upon the particular zygote and functions of the exogenous genetic material and will be readily apparent to one in the art, because the genetic material, including the exogenous genetic material, of the resulting zygote must be biologically capable of initiating and maintaining the differentiation and development of the zygote into a functional organism. From a biological consideration, relating to mitosis, when the exogenous genetic material is a chromosome, the amount inserted will not be greater than one chromosome and preferably will be less than one chromosome.

The number of copies of the DNA sequences which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of a gene, in order to insure that one copy is functional. Generally, there is no advantage to having more than one functioning copy of each of the inserted exogenous DNA sequences unless an enhanced phenotypic expression of the exogenous DNA sequences is desired. There are instances where more than one functional copy of the exogenous DNA sequences may not be desirable, for example, when the exogenous DNA sequences work in conjunction with endogenous DNA sequences of the organism to produce a particular product. A specific example, in the case of a mammal, is the insertion of sufficient copies of an exogenous gene coding for β-globin (without concomitant insertion of the α-globin gene) to produce many functional β-globin genes in the genetically transformed organism. This can cause the organism to have a form of thalassemia due to a disproportionate production of β-globin compared to α-globin.

The particular composition or form of the exogenous genetic material is not critical. If a particular trait is desired to be incorporated into an organism, then the genetic material needs to contain the DNA sequence or sequences, or gene or loci, which code for the trait. Thus, whether the exogenous genetic material is a a whole chromosome, a portion of a chromosome, purified or unpurified native DNA or synthetic or semi-synthetic DNA or chromosomal complexes is dependent upon the particular trait or traits sought to be incorporated into the zygote and ease of obtaining that trait. Techniques for obtaining DNA sequences by gene excising, splicing, synthesis, isolation, purification and cloning as well as enzymes used in Such processes, vehicles and hosts for cloning of recombinant DNA, screening and selection of cloned DNA and detection and analysis of expression of cloned genes are known in the art. *Methods in Enzymology: Recombinant DNA*, Vol. 68, edited by Ray Wu, Academic Press, Inc., New York, 1979, is an example of a reference which discusses many of these techniques.

Depending upon the particular trait or traits being inserted into the zygote, it maybe desirable to include the control sequences of the genetic material responsible for controlling the gene(s) coding for the trait, particularly when the genotype of the zygote contains no similar gene whose control region could be used to regulate the gene or when greater genetic activity is desired. In some instances it may be desirable, to include a control region, e.g., an artificial one spliced to the exogenous gene, which will activate the gene when the organism is exposed to a different stimulus other than the natural stimulus of the gene. For example, a growth hormone gene inserted into a bovine zygote could be attached to a control gene which is responsive to a molecule which could be added to the feed of the animal. Thus, each time the animal ingested the molecule, the growth hormone gene would be activated.

Techniques for obtaining immature germ cells, gametes and zygotes, for parthogenesis and for in vitro and in vivo development of zygotes are well known. The conditions under which the exogenous genetic material is added or inserted should be such as to maintain the cells in a viable state and will grossly mimic the natural in vivo development conditions of the cells. After the exogenous genetic material is inserted and the zygote formed, the zygote is allowed to develop under in vitro conditions. In the case of some animal zygotes, for example, mammals, it will be necessary to complete the development of the zygote in vivo by implanting it into a foster mother. It is preferred that the implantation occurs at the morula or blastocyst stage of development.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

EXAMPLE

Procedure

Fertilized eggs at early pronuclear stage, the male and female pronuclei being separated and distinguishable within the cytoplasm, were collected from the oviducts of C57BL/6J female mice which had been mated to LT/Sv males. After removing the surrounding cumulus cells in culture medium containing 1 milligram (mg) bovine testis hyaluronidase per milliliter (ml) culture medium, as described in *Biol. Reprod.,* 8:420–426 (1973), pooled zygotes from several females were washed in fresh medium and stored, until micromanipulation, in a depression slide containing culture medium overlayered with paraffin oil in an atmosphere of 5 percent carbon dioxide, 5 percent oxygen and 90 percent nitrogen (percentages are based on volume) at 37° C.

The hybrid plasmid Z-pCR1/Rchr βG-1, containing rabbit β-globin, was extracted from *E. Coli HB*101 containing the hybrid plasimd using a lysozyme, Triton x-100 ethylenediaminetetracetic acid lysis procedure and was subsequently purified by cesium chloride-Ethidium bromide density gradient centrifugation followed by agarose gel electrophoresis in a low melting point agarose. The purified plasmid which contained the rabbit β-globin gene was then digested with Hha I restriction endonuclease (Plasmid pCR1 has numerous Hha I sites while the β-globin has none). The 6200 base pair β-globin gene DNA fragment was then purified by electrophoresis of the Hha I digest of the plasmid in low melting point agarose. The β-globin fragment DNA band was extracted from the agarose by melting the gel at 60° C. followed by extraction with phenol. The thus obtained β-globin gene fragments contained approximately 50 micrograms of DNA per milliliter. The β-globin gene sequence contained a 223 base pair control sequence upstream from the cap site of the structural gene which included a TATA sequence (Goldberg, M., Ph.D. thesis, Stanford University (1979)) and-the CAAT sequences (Efstratiadis, A., et al, *Cell,* 21:653–668 (1980)).

Injection pipets with an external diameter of about 1 micrometer and holding pipets with an external diameter of about 60–70 micrometers were prepared from pyrex tubing as described in *Proc. Natl. Sci. U.S.A.,* 74:5657–5661 (1977). Manipulation of the pipets for holding and subsequent injection of the zygote was accomplished using Leitz micro-manipulators and paraffin oil filled Hamilton microsyringes. A small drop each of culture medium with 5–6 zygotes and of rabbit β-globin chromosomal gene solution were placed on a special microscope slide and covered with paraffin oil. Approximately 10 picoliters of β-globin gene solution, which is approximately 20,000 DNA sequences, was drawn into the injection pipet which was then moved to the drop of culture medium containing the eggs. A zygote was positioned onto the holding pipet so that the male pronucleus was in juxta-position to the injection pipet for subsequent injection of the β-globin gene suspension into the pronucleus. After microinjection of all of the zygotes, they were removed from the drop of medium on the microscope slide and placed in culture tubes where they were allowed to develop for five days. The conditions of the preimplantation development is described in *Biol. Reprod.,* 8:420–426 (1973). Eggs developing to morulae or blastocysts were transplanted into uteri of $F_1$ hybrid, C57BL/6J× SJL/J, foster mouse mothers who were at day three of pseudopregnancy. The foster mothers carried the implanted embryos to term. The preimplantation and postimplantation development of $F_1$ hybrid, C57BL/6J×LT/Sv zygotes after microinjection of rabbit β-globin chromosomal gene into the male pronucleus is given in Table 1.

TABLE 1

| | |
|---|---|
| Number zygotes injected | 143 |
| Number eggs cleaving | 139 |
| Number morulae and blastocysts transplanted to foster mothers | 120 |
| Number foster mothers | 12 |
| Number foster mothers pregnant | 8 |
| Number offspring born | 28[a] |

[a]Eighteen males and ten females.

Analyses

The presence of rabbit β-globin DNA sequences in the nucleic genetic material of mice developed from the rabbit β-globin gene microinjected $F_1$ hybrid mouse zygote was demonstrated by the specific hybridization of plasmid Z-pCR1/RchrβG-1 to the liver DNA of these mice.

Hemoglobin was prepared from blood samples taken from each of the mice developed from the rabbit β-globin gene microinjected $F_1$ hybrid mouse zygotes and analyzed by agarose immunodiffusion against $F_1$ hybrid (C57BL/6J×LT/Sv) mouse antirabbit hemoglobin antiserum. The three samples which showed the most distinct positive reaction with the antiserum were pooled and used in the immunodiffusion analyses hereinafter described.

Agarose gel immunodiffusion, using $F_1$ hybrid mouse antirabbit hemoglobin antiserum showed a major band of precipitation with the control rabbit hemoglobin, a major band of precipitation with the hemoglobin prepared from the $F_1$ hybrid mice that developed from zygotes microinjected with purified rabbit β-globin gene sequences and no evidence of precipitation with hemoglobin prepared from normal $F_1$ hybrid mice. The major precipitation band between the microinjected mouse hemoglobin and the mouse antirabbit hemoglobin antiserum established that the erythrocytes of the mice developed from the β-globin gene microinjected zygotes contain a molecular species which reacts specifically with antiserum produced against rabbit hemoglobin.

The agarose gel immunodiffusion shows identity between one of the dissociated rabbit globin chains and a molecular species present in the erythrocytes of mice developed from the β-globin gene microinjected zygotes.

In order to establish that the immunoprecipitation band between the $F_1$ hybrid mouse antirabbit hemoglobin antiserum and the hemoglobin preparation from mice resulting from zygotes microinjected with rabbit β-globin genes is the result of a specific immunological reaction, a control immunodiffusion analysis was performed using $F_1$ hybrid mouse antirabbit hemoglobin antiserum which had been absorbed by passage through a column containing rabbit hemoglobin bound to an inert matrix. The absorbed antiserum, did not react with either rabbit hemoglobin or the hemoglobin from the mice which developed from the microinjected zygotes.

In addition to the immuno analyses described above, the hemoglobin of the mice that had been genetically transformed with rabbit β-globin gene was isoelectrically focused. The isoelectric focusing revealed that their hemoglobin contained a subtraction which is not the same as the hemoglobin of the control mice or of a rabbit and thus appears to be a new hemoglobin. In view of the isoelectric focusing results and the immunological activity of the hemoglobin of the genetically transformed mice with the mouse antirabbit hemoglobin antiserum, the hemoglobin of the genetically transformed mice is comprised apparently of at least one rabbit β-globin and mouse α-globins.

The mice that had been genetically transformed with the rabbit β-globin gene also have an abnormally high percent, about 6 percent, of reticulocytes in their blood. The control mice of the same inbred species and age have a reticulocyte concentration of about 0.5 percent of their blood cells. The high percentage of reticulocytes is indicative of thalassemia, an anemia resulting from the presence of excess rabbit β-globin.

Finally, several of the mice that were genetically transformed by the rabbit β-globin gene have produced offspring which also phenotypically express the rabbit β-globin gene.
Preparation of Hemoglobins and Antisera used in the Immunological Analyses Each hemoglobin preparation was prepared as a purified hemolysate with blood from New Zealand white rabbits, normal $F_1$ hybrid (C57BL/6J×LT/Sv) mice and $F_1$ hybrid (C57BL/6J×LT/Sv) mice developed from zygotes microinjected with rabbit β-globin gene DNA sequences. The erythrocytes for each hemoglobin preparation were washed exhaustively with phosphate buffered saline, lysed in distilled water and centrifuged at 12,000 times gravity for 10 minutes to remove the erythrocyte membrane. Prior to application of the hemoglobin sample to agarose immunodiffusion plates, the hemoglobin solutions were filtered through a 0.45 micro filter and adjusted to a concentration of 100 mg/ml.

The mouse antirabbit hemoglobin antiserum was raised in $F_1$ hybrid (C57BL/6J×LT/Sv) mice. Rabbit hemoglobin in distilled water was emulsified with an equal volume of complete Freund's adjuvant and each animal received a 500 microgram priming dose, subcutaneously, divided among four sites. After one and two weeks all animals received second and third injections of 10 micrograms of rabbit hemoglobin emulsified in incomplete Freund's adjuvant administered subcutaneously and intraperitoneally, respectively. After four weeks each animal was injected intraperitoneally with 600 micrograms of rabbit hemoglobin in complete Freund's adjuvant. The immunized animals were bled after week five and the serum separated, tested against rabbit hemoglobin and preserved in the presence of sodium azide.

Free rabbit globin chains were prepared from a rabbit hemolysate by acetone extraction of the heme iron complex resulting in dissociation of the α and β protein subunits. Five hundred micrograms of packed, washed, rabbit erythrocytes were lysed in 2 milliliters of distilled water and the resulting hemolysate dripped slowly into a stirred solution of acetone and 1.2 milliliters of concentrated HCl at −70° C. The resulting precipitated rabbit globin chains were allowed to stand for 15 minutes at −70° C. in the extraction mixture after which they were washed twice with −20° C. acetone and dried under vacuum at liquid nitrogen temperatures. The dried precipitate was dissolved in 2 milliliters of distilled $H_2O$ and dialysed exhaustively against phosphate buffered saline.

Rabbit hemoglobin, 30 milligrams, was coupled to Sepharose 4B Gel beads by reaction with 1 gram washed CNBr-activated Sepharose 4B from Pharmacia Fine Chemicals, Inc. in 0.1M $NaHCO_3$ and 0.5M NaCl at a pH of 8.0, for 3 hours at room temperature. Following the coupling reaction, the remaining active groups on the gel beads were reacted with 1M Tris, pH 8.0, and the hemoglobin Sepharose gel was washed exhaustively to remove any unbound hemoglobin. The gel-immobilized rabbit hemoglobin was used to prepare a miniature column for the selective removal of antirabbit hemoglobin antibodies from immunized mouse serum.

Reactivity of transformed mouse hemoglobin antigens with mouse antirabbit hemoglobin antiserum was detected by double diffusion analysis on 1 percent agarose slides. Antigen wells contained 15 microliters of each hemoglobin antigen (100 mg/ml) and the antibody well contained 15 microliters of antirabbit hemoglobin antiserum. Each well was refilled twice during the 24 hour incubation at 37° C. Reactivity was characterized by the production of a band of precipitation between the hemoglobin of the transformed mice and the mouse antirabbit hemoglobin antiserum.

This invention has been described with particular reference to a specific embodiment thereof, but it will be understood that variations and modifications can be effected within the spirit of the invention.

What is claimed is:

1. A nonhuman transgenic mammal whose somatic and germ cells contain exogenous genetic material, wherein said material does not include any virus-specific DNA and includes at least one heterologous gene and a transcriptional control sequence operably associated therewith, wherein said gene is expressed at a detectable level in a plurality of said somatic cells or said germ cells, where said genetic material is selected so that the normal development of the embryo to term is not prevented by said material, where said mammal is selected from the group consisting of rodents, rabbits, goats, pigs, cattle, and sheep.

2. A nonhuman mammal according to claim 1, wherein all cells of the mammal contain said gene operably linked to a control sequence.

3. A nonhuman mammal according to claim 1, at least some of said cells being germ line cells, where said mammal has transmitted the phenotype conferred by said gene to at least one of its progeny.

4. A nonhuman mammal which is descended from an ancestral transgenic mammal according to claim 1, said descendant mammal also expressing said gene at a detectable level.

5. The nonhuman mammal of claim 1, said control sequence being responsive to a substance which may be added to the feed of the animal and which, after ingestion, will cause activation of said gene.

6. A nonhuman mammal characterized as having somatic and germ cells that contain exogenous genetic material that does not include any virus-specific DNA, said material including at least one heterologous gene and a transcriptional control sequence operably associated therewith, said gene being expressible at a detectable level in a plurality of said somatic cells or said germ cells of said mammal under the control of said control sequence, said genetic material being selected so that the normal development of the embryo to term is not prevented by such material, said mammal having been obtained by the following steps:

(a) introducing exogenous genetic material into a pronucleus of a mammalian zygote by microinjection, said genetic material including at least one heterologous gene and a control sequence operably associated therewith, thereby obtaining a genetically transformed zygote;

(b) transplanting an embryo derived from the genetically transformed zygote into a pseudopregnant female; and (c) allowing the embryo to develop to term;

or a mammal descended from a transgenic mammal so produced which retains the heterologous gene in expressible form, where said mammal is selected from the group consisting of rodents, rabbits, goats, pigs, cattle, and sheep.

7. A nonhuman mammal according to claim 1, wherein said embryos and said gene are from different species of mammal.

8. A method of producing a polypeptide or protein which comprises:

(a) producing a mammal capable of expressing said polypeptide or protein at a detectable level by a method which comprises
  (i) introducing exogenous genetic material that does not include any virus-specific DNA into a pronucleus of a mammalian zygote by microinjection, said genetic material including at least one heterologous gene and a transcriptional control sequence operably associated therewith, thereby obtaining a genetically transformed zygote;
  (ii) transplanting an embryo from the genetically transformed zygote into a pseudopregnant female; and
  (iii) allowing the embryo to develop to term; where said gene and control sequence are selected so that the gene is not activated in such manner and degree as would prevent normal development of the embryo to term; and said polypeptide or protein is producible in a cell of said mammal which bears said gene, as a result of the expression of said gene under the control of said control sequence, and where said mammal, absent said exogenous genetic material, is unable to produce said polypeptide or protein; and (b) expressing said gene in said mammal, or progeny thereof which retain said gene in expressible form, thereby producing said polypeptide or protein at a detectable level, where said mammal is selected from the group consisting of rodents, rabbits, goats, pigs, cattle, and sheep.

9. The method of claim 8 wherein the transcriptional control sequence is not the native control sequence of said gene.

10. The method of claim 8 wherein the control sequence is a vertebrate globin control sequence.

11. The method of claim 8 in which the polypeptide or protein is a vertebrate globin or a hemoglobin.

12. The method of claim 8 in which the material is introduced into the male pronucleus of an egg having a separate female and male pronucleus.

13. The method of claim 8 in which the zygote is allowed to develop in vitro to the morula or blastocyst stage prior to transplantation.

14. The method of claim 8 further comprising recovering said polypeptide or protein.

15. The method of claim 14 wherein said polypeptide or protein is recovered from the blood of said mammal.

16. The mammal of claim 1 wherein the transcriptional control sequence is not the native control sequence of said gene.

17. The method of claim 6 wherein the transcriptional control sequence is not the native control sequence of said gene.

18. The mammal of claim 1 wherein the exogenous genetic material is recombinant DNA.

19. The mammal of claim 1 wherein the transcriptional control sequence is regulatable.

20. The mammal of claim 1 wherein the transcriptional control sequence is a vertebrate globin control sequence.

21. The mammal of claim 1 wherein the gene encodes a vertebrate globin.

22. The mammal of claim 1 wherein the genetic material is free of any viral DNA sequences encoding a protein required for viral integration, and is also free of any plasmid DNA sequences required for autonomous replication of the plasmid.

23. The mammal of claim 6 wherein the exogenous genetic material is recombinant DNA.

24. The mammal of claim 6 wherein the transcriptional control sequence is regulatable.

25. The mammal of claim 6 wherein the transcriptional control sequence is a vertebrate globin control sequence.

26. The mammal of claim 6 wherein the gene encodes a vertebrate globin.

27. The mammal of claim 6 wherein the genetic material is free of any viral DNA sequences encoding a protein required for viral integration, and is also free of any plasmid DNA sequences required for autonomous replication of the plasmid.

28. The mammal of claim 1 which expresses the gene under predetermined conditions.

29. The method of claim 11 in which the polypeptide is a mammalian globin.

30. The method of claim 29 in which the polypeptide is a beta globin.

31. The method of claim 29 wherein the control sequence is a globin control sequence.

32. The mammal of claim 1 in which the polypeptide is a mammalian globin.

33. The mammal of claim 32 in which the polypeptide is a beta globin.

34. The mammal of claim 32 in which the control sequence is a mammalian globin sequence.

35. The mammal of claim 1 wherein the mammal is a rodent.

36. The mammal of claim 1 wherein the mammal is a mouse.

37. The mammal of claim 1 wherein the mammal is a mammal used in agriculture.

38. The mammal of claim 1 wherein the mammal is a mouse, rat, rabbit, goat, pig.

39. The mammal of claim 1 in which the promoter is a mammalian globin promoter.

40. The mammal of claim 1 in which the promoter is a mammalian beta globin promoter.

41. The mammal of claim 21 in which the promoter is a mammalian globin promoter.

42. The mammal of claim 32 in which the promoter is a mammalian globin promoter.

43. The mammal of claim 33 in which the promoter is a mammalian beta globin promoter.

44. The mammal of claim 1 in which the promoter is endogenous to the gene.

45. The mammal of claim 44 in which the gene is a vertebrate globin gene.

46. The mammal of claim 38 in which the gene is a mammalian globin gene.

47. The mammal of claim 45 in which the promoter is a mammalian globin promoter.

48. The mammal of claim 46 in which the promoter is a mammalian globin promoter.

49. The method of claim 8 wherein the mammal is a rodent.

50. The method of claim 8 wherein the mammal is a mouse.

51. The method of claim 8 wherein the mammal is a mammal used in agriculture.

52. The method of claim 8 wherein the mammal is a mouse, rat, rabbit, goat, pig.

53. The method of claim 8 in which the promoter is a mammalian globin promoter.

54. The method of claim 8 in which the promoter is a mammalian beta globin promoter.

55. The method of claim 8 in which the promoter is a mammalian globin promoter.

56. The method of claim 29 in which the promoter is a mammalian globin promoter.

57. The method of claim 30 in which the promoter is a mammalian beta globin promoter.

58. The method of claim 8 in which the promoter is endogenous to the gene.

59. The method of claim 52 in which the gene is a vertebrate globin gene.

60. The method of claim 52 in which the gene is a mammalian globin gene.

61. The method of claim 59 in which the promoter is a mammalian globin promoter.

62. The method of claim 60 in which the promoter is a mammalian globin promoter.

63. The mammal of claim 1, wherein said gene is a preselected gene.

64. The method of claim 8, wherein said gene is a preselected gene.

* * * * *